(12) United States Patent
Werth

(10) Patent No.: US 7,922,213 B2
(45) Date of Patent: *Apr. 12, 2011

(54) BARB CLAMP WITH SMOOTH BORE

(75) Inventor: Albert Werth, Kewadin, MI (US)

(73) Assignee: Twin Bay Medical, Inc., Williamsburg, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/411,852

(22) Filed: Mar. 26, 2009

(65) Prior Publication Data

US 2009/0179422 A1   Jul. 16, 2009

Related U.S. Application Data

(63) Continuation-in-part of application No. 12/034,279, filed on Feb. 20, 2008, which is a continuation-in-part of application No. 10/963,457, filed on Oct. 13, 2004, now abandoned.

(60) Provisional application No. 60/512,231, filed on Oct. 17, 2003.

(51) Int. Cl.
 *F16L 33/207* (2006.01)
(52) U.S. Cl. ............. 285/243; 285/3; 285/242; 285/259
(58) Field of Classification Search ............. 285/3, 242, 285/243, 255, 256, 259
See application file for complete search history.

(56) References Cited

U.S. PATENT DOCUMENTS

| | | | |
|---|---|---|---|
| 36,410 A | 9/1862 | Jucket | |
| 1,390,564 A * | 9/1921 | Knorr | 285/243 |
| 2,868,564 A | 1/1959 | Arras | |
| 2,940,778 A | 6/1960 | Kaiser | |
| 2,958,549 A | 11/1960 | Spafford | |
| 3,325,194 A | 6/1967 | Grawey | |
| 3,589,752 A | 6/1971 | Spencer et al. | |
| 3,653,692 A | 4/1972 | Henson | |
| 3,868,130 A * | 2/1975 | Schwertner et al. | 285/243 |
| 4,205,417 A * | 6/1980 | Mackal | 24/537 |
| 4,303,263 A | 12/1981 | Legris | |

(Continued)

FOREIGN PATENT DOCUMENTS

EP   0515930 A1   12/1992

(Continued)

OTHER PUBLICATIONS http://www.biopuretech.com/flow-path-components/s-bio-barbs.html.

(Continued)

*Primary Examiner* — James M Hewitt
(74) *Attorney, Agent, or Firm* — Young Basile

(57) ABSTRACT

A barb clamp for use with a flexible tube is taught, the flexible tube having an inner bore defined by a predetermined inner diameter for providing a fluid flow path. The barb clamp includes a barb connector having the same predetermined inner diameter as the flexible tube and a tapered end insertable into the tube. A sleeve and collet lock over the tubing and barb connector to prevent liquid material entering between the barb and tube. The tapered end of the barb connector terminates at a point so that there is no transition between the inner diameter of the tube and the inner diameter of the barb connector to provide no pressure differential in the tube between the outside and inside of the barb clamp.

12 Claims, 8 Drawing Sheets

U.S. PATENT DOCUMENTS

| | | | |
|---|---|---|---|
| 4,412,693 A | | 11/1983 | Campanini |
| 4,564,222 A | | 1/1986 | Loker et al. |
| 4,632,435 A | | 12/1986 | Polyak |
| 4,723,948 A | | 2/1988 | Clark et al. |
| 4,796,856 A | | 1/1989 | Munini |
| 4,880,414 A | | 11/1989 | Whipple |
| 4,890,866 A | | 1/1990 | Arp |
| 4,906,030 A | | 3/1990 | Yokomatsu et al. |
| 4,932,689 A | * | 6/1990 | Bradley ................. 285/255 |
| 5,074,600 A | | 12/1991 | Weinhold |
| 5,076,614 A | | 12/1991 | Yokomatsu et al. |
| 5,149,145 A | * | 9/1992 | Yokomatsu et al. .......... 285/101 |
| 5,150,924 A | * | 9/1992 | Yokomatsu et al. .......... 285/101 |
| 5,150,925 A | * | 9/1992 | Yokomatsu et al. .......... 285/101 |
| 5,172,943 A | * | 12/1992 | Shimada .................. 285/323 |
| 5,240,289 A | | 8/1993 | Gottling et al. |
| 5,275,447 A | | 1/1994 | McNab |
| 5,361,806 A | | 11/1994 | Lalikos et al. |
| 5,476,291 A | | 12/1995 | Reneau |
| 5,536,258 A | | 7/1996 | Folden |
| 5,584,513 A | | 12/1996 | Sweeney et al. |
| 5,709,413 A | | 1/1998 | Salyers |
| 5,725,447 A | | 3/1998 | Friedmann et al. |
| 5,882,047 A | | 3/1999 | Ostrander et al. |
| 5,909,902 A | | 6/1999 | Seabra |
| 5,984,378 A | | 11/1999 | Ostrander et al. |
| 6,010,162 A | | 1/2000 | Grau et al. |
| 6,155,610 A | | 12/2000 | Godeau et al. |
| 6,170,887 B1 | | 1/2001 | Salomon-Bahls et al. |
| 6,254,144 B1 | * | 7/2001 | Hagan ..................... 285/243 |
| 6,435,568 B1 | | 8/2002 | Fukano et al. |
| 6,796,586 B2 | * | 9/2004 | Werth ..................... 285/243 |
| 6,860,521 B2 | | 3/2005 | Berg |
| 6,908,120 B2 | | 6/2005 | Tomita et al. |
| 7,090,257 B2 | * | 8/2006 | Werth ..................... 285/243 |
| 7,118,136 B2 | * | 10/2006 | Ohya ..................... 285/3 |
| 7,370,889 B2 | | 5/2008 | Maunder et al. |
| 7,661,721 B2 | * | 2/2010 | Mittersteiner et al. ........ 285/243 |
| 2003/0006610 A1 | * | 1/2003 | Werth ..................... 285/243 |
| 2003/0047943 A1 | | 3/2003 | Berg |
| 2003/0193190 A1 | * | 10/2003 | Werth ..................... 285/243 |
| 2004/0232697 A1 | | 11/2004 | Tomita et al. |
| 2005/0082826 A1 | * | 4/2005 | Werth ..................... 285/243 |
| 2008/0169646 A1 | | 7/2008 | Werth |
| 2009/0179422 A1 | * | 7/2009 | Werth ..................... 285/243 |
| 2009/0212559 A1 | * | 8/2009 | Werth ..................... 285/243 |

FOREIGN PATENT DOCUMENTS

| | | |
|---|---|---|
| EP | 0762034 A1 | 3/1997 |
| FR | 1052094 | 1/1954 |
| JP | 06159573 A | 6/1994 |
| JP | 2002525542 A | 8/2002 |
| JP | 2004347074 A | 12/2004 |
| KR | 1019910008238 B1 | 10/1991 |
| KR | 1019930009058 B1 | 9/1993 |
| KR | 200269757 Y1 | 3/2002 |
| KR | 200302163 Y1 | 1/2003 |
| WO | 9813637 A1 | 4/1998 |
| WO | 2005037343 A2 | 4/2005 |

OTHER PUBLICATIONS

Written Opinion of the ISA and International Search Report dated Aug. 25, 2009 from the corresponding International Patent Application No. PCT/US2009/031257 filed Jan. 16, 2009.

EP Search Report (Dated: Oct. 21, 2009); Appl. No. 04795367.4; Applicant: Twin Bay Medical, Inc.

Notification, Search Report and Written Opinion of the International Searching Authority dated Aug. 6, 2010 from the corresponding International Application No. PCT/US2010/020458 filed Jan. 8, 2010.

Examination Report dated Aug. 16, 2010 from the corresponding EP Patent Application No. 04795367.4-1523 filed Oct. 14, 2004.

International Search Report and Written Opinion, dated Oct. 28, 2005, from the corresponding International Application No. PCT/US04/34190.

* cited by examiner

BARB CLAMP WITH SMOOTH BORE

CROSS-REFERENCE TO RELATED APPLICATIONS

This application is a continuation-in-part application of U.S. patent application Ser. No. 12/034,279, a pending application filed Feb. 20, 2008, which is hereby incorporated by reference.

U.S. patent application Ser. No. 12/034,279 in turn is a continuation-in-part application of U.S. patent application Ser. No. 10/963,457 filed on Oct. 13, 2004 and now abandoned, which claims priority of provisional patent application 60/512,231 filed on Oct. 17, 2003 and now expired, both of which are hereby incorporated by reference.

TECHNICAL FIELD

The present invention relates to a fastening device for a tubular body.

BACKGROUND

The transfer of fluid through flexible tubing is widely used in various environments. Ultimately, the flexible tubing is connected to the source of the gaseous or liquid fluid, the delivery site of the fluid, or to flexible tubing. At the ends of the flexible tubing, it is necessary to provide a secure and leak proof connections. Although these requirements are necessary in all environments using flexible tubing, it is critical in the medical and pharmaceutical, food and beverage fields. In the medical and pharmaceutical fields flexible tubing and associated connections are used for luer fittings, quick connects, or sanitary fittings such as used in blood pumps, oxygen concentrators, sleep apnea equipment, medical transport containers, IV bags, etc. In some environments, and especially in the medical field, it is imperative to absolutely prohibit any liquids from getting between the tube and the connection fitting at the connection point. Any gap or abrupt change at the point of connection will entrap fluid, e.g. bio, blood, drugs, foodstuff, etc. This entrapment can cause growth of harmful bacteria.

SUMMARY

Embodiments of a barb clamp for a flexible tube having a predetermined inner diameter defining a passageway therein and an outer surface are disclosed herein. In one such embodiment, the barb clamp includes a barb connector having a tubular configuration with a first end for disposing within an end of the tube. The barb connector has a smooth inner bore with a constant diameter defining a fluid passageway therein, and the constant diameter of the inner bore is equal to the predetermined inner diameter of the flexible tube.

The barb clamp also includes a cylindrical collet and a cylindrical sleeve. The cylindrical collet has a through aperture slidable over the first end of the barb connector. The collet has a first end, a second end, and inner and outer surfaces. The inner surface of the collet has a circumferential ridge at the first end of the through aperture and the outer surface of the collet has a bi-level configuration wherein the diameter of the outer surface adjacent the first end is less than the diameter of the outer surface adjacent the second end defining a ledge therebetween.

The cylindrical sleeve has a through center aperture for slidably receiving the collet and a first and a second end. The second end of the sleeve is connected to the second end of the collet by a frangible meniscus of material. Further, The through center aperture of the sleeve is defined by an inner surface. The inner surface has a first circumferential portion, a second circumferential portion, a third circumferential portion and a fourth circumferential portion. The first circumferential portion has an expanded diameter and is located adjacent to the second end of the sleeve. The frangible meniscus is connected the first circumferential portion. The second circumferential portion is located adjacent to the first circumferential portion and ramps to a reduced diameter portion defined by the third circumferential portion. The third circumferential portion terminates at a ledge at a midpoint of the sleeve.

Other embodiments are described in additional detail hereinafter.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
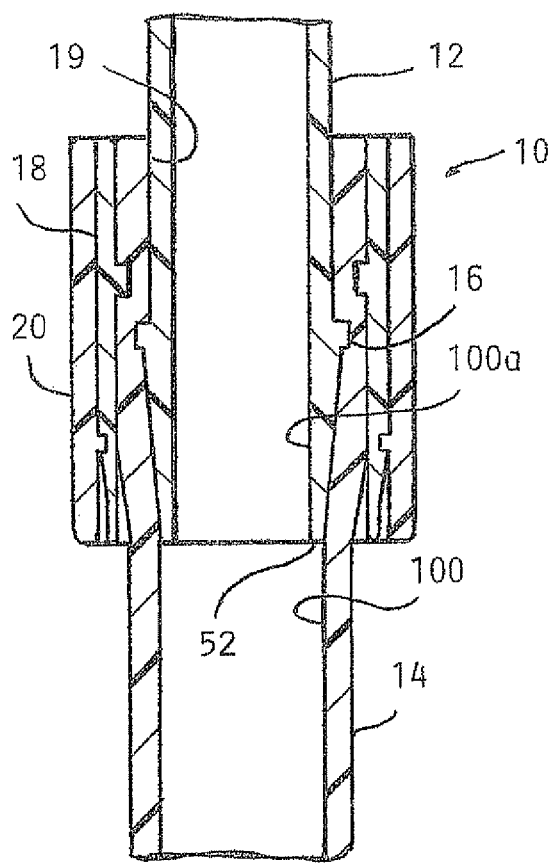
FIG. 1 is a sectional view of a current barb clamp.
Figure 2:
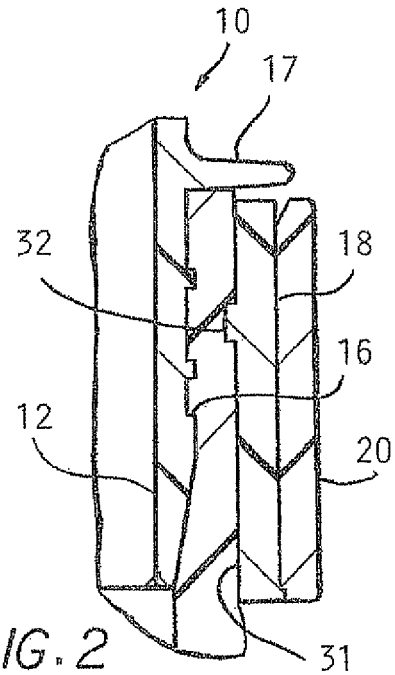
FIG. 2 is a partial sectional view of an alternative to the current barb clamp.

FIGS. 1 and 2 show the current barb clamp connector 10 for coupling a barbed fitting 12 and a flexible tube 14 and discussed hereafter. The barb fitting 12 is generally made of a non-metal material which allows it to be heat welded to a propylene or ethylene medical or pharmaceutical bag. The same and similar materials can be used for biotech, pharmaceutical, medical, and foodstuff fitting connections and manifold applications. The fitting can also be made from other plastics and stainless steel when required. As seen in FIGS. 1 and 2, the barbed fitting 12 may encompass different configurations but will generally include at least one expanded or barbed end 16 for a 360° radial compression connection to the flexible tube 14. If the barb clamp 10 is to be used in a medical or pharmaceutical environment, the barb fitting 12 is preferably made from an FDA (Food and Drug Administration) approved polypropylene, silicone, TPE, TPR, etc. The barb fitting 12 may also include a flanged portion 17 which defines a stop for the barb clamp 10.

The barb clamp 10 includes a collet 18 and a sleeve 20. The collet 18 and the sleeve 20 are as shown in FIGS. 1-6 and are similar to the collet and sleeve discussed in U.S. patent application Ser. No. 10/100,519 filed on Mar. 18, 2002, now U.S. Pat. No. 6,796,586 issued on Sep. 28, 2004.

The collet 18 is an essentially annular member having a through aperture 19 for receiving the end of a tube 14 therein. The sleeve 20 is also an annular member with a through aperture 21 for receiving the end of the tube 14 as well as having a diameter for also receiving the collet 18 therein.

Figure 3:
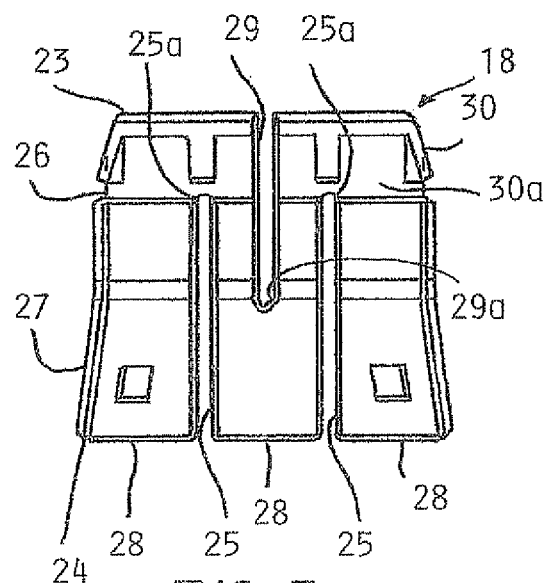
FIG. 3 is an elevational view of a collet for the current barb clamp.
Figure 5:
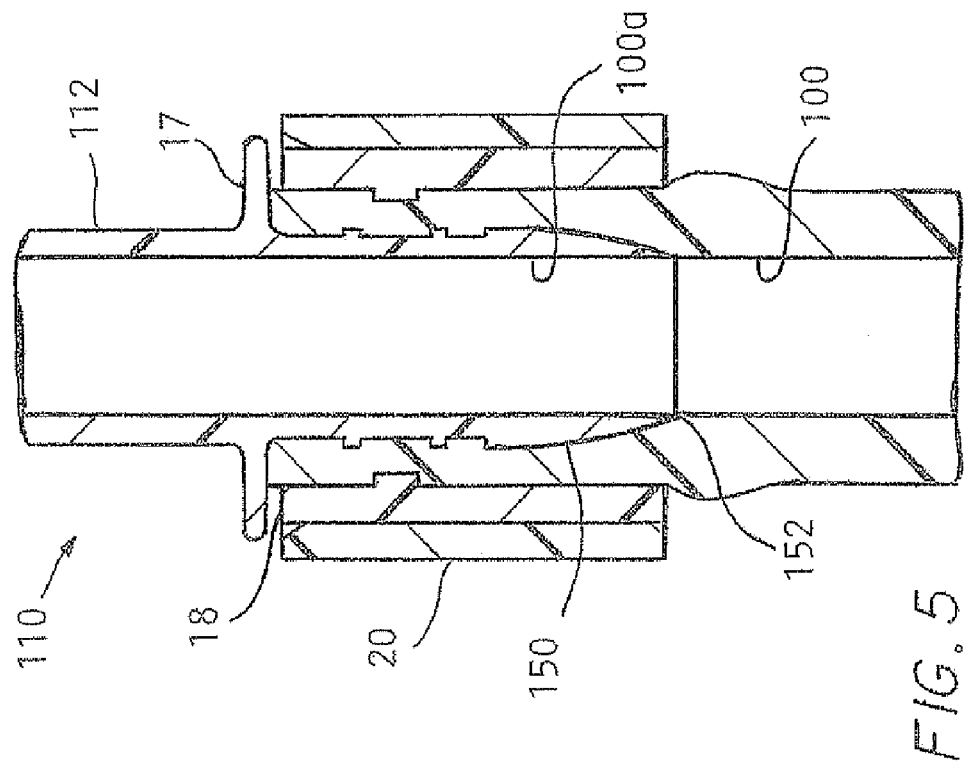
FIG. 5 is a sectional view of an improved barb clamp according to the present invention.
Figure 7:
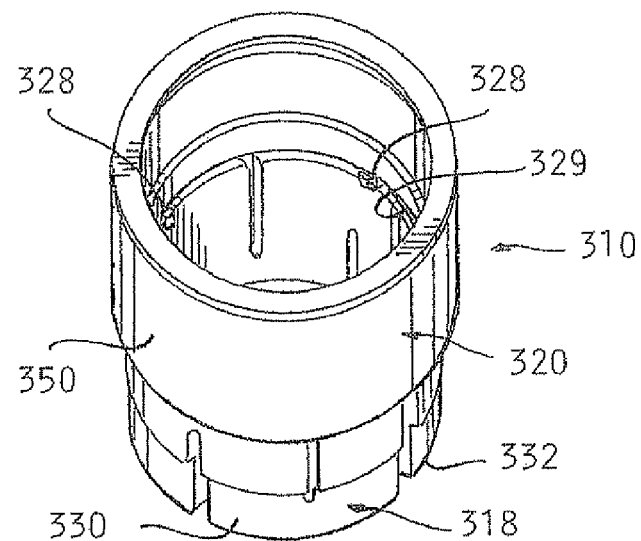
FIG. 7 is a perspective view of another alternative embodiment of the improved collet and sleeve.
Figure 8:
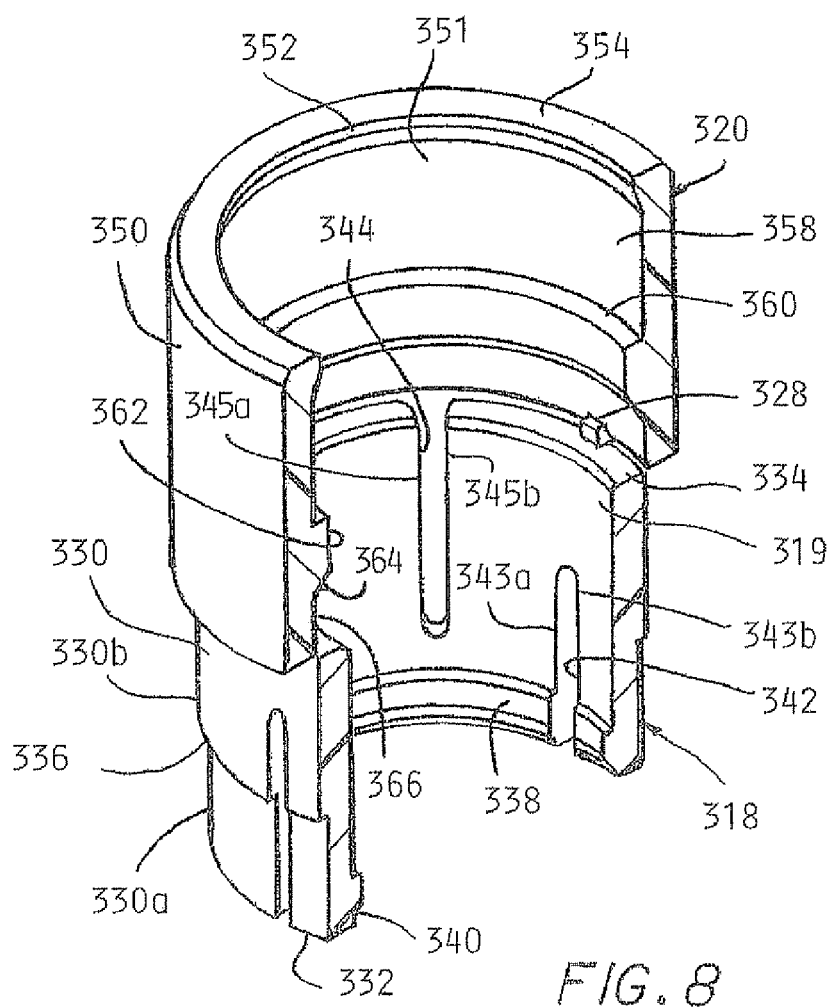
FIG. 8 is a perspective view of the embodiment shown in FIG. 7 having a portion sectioned off to illustrate certain figures.
Figure 9:
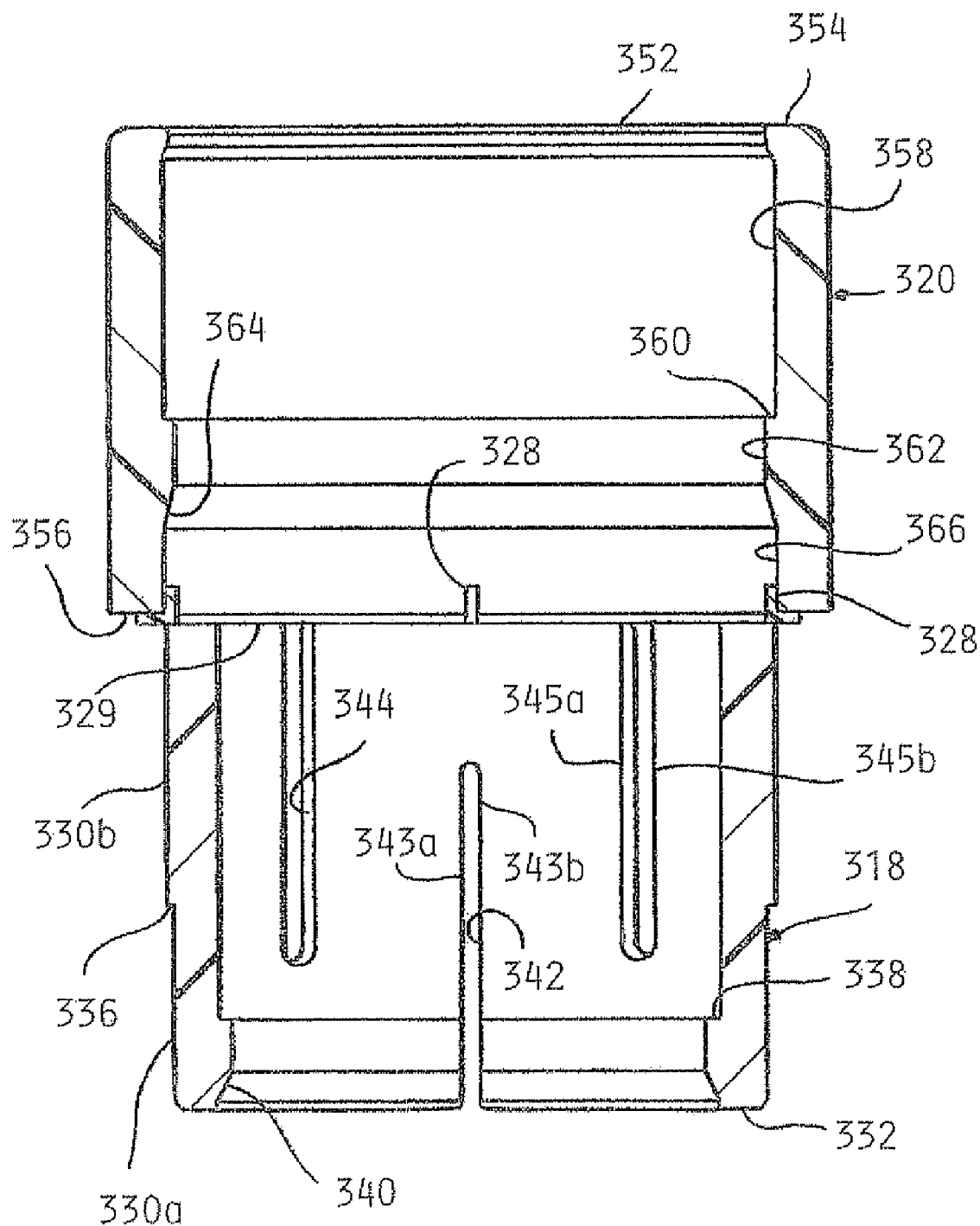
FIG. 9 is a sectional view of the collet and sleeve of the barb clamp shown in FIG. 7 in an unlocked position.

Looking at FIG. 3 the collet 18 has an exterior surface 22 providing resilient means for radially contracting around the tube 14. The collet 18 has a first end 23 forming a discontinuous annular ring. Along the exterior surface 22 and adjacent to the first end 23 is an annular groove 26. Moving toward the second end 24 and beyond the annular groove 26, the collet forms eight resilient tangs 28. The tangs 28 radially flare out or expand slightly at the second end 24 of the collet 18. The tangs 28 begin to flare approximately at the mid section 27 of each tang 28. The tangs 28 are formed by narrow through slots 25 extending from the second end 24 and terminating at the annular groove 26. The slots 25 are shown in FIGS. 3 and 5 with rounded termination ends 25a, however, the termination ends 25a may have pointed ends, (not shown).

A small ramping ledge 30 projects above each termination end 25a of the narrow through slots 25. The small ledges 30 provide added strength to the collet and also provide a stop means for the sleeve 20, as will be discussed hereinafter. Between each small ledge 30 there is a recessed planar portion 30a extending into the annular groove 26. The eight tangs 28 form a resilient seal which allow the tangs to contract around a tubular member 14. Between every other tang 28 there is a through slot 29 which extends from the first end 23 to the mid-section 27 of the associated tang 28. The through slots 29 may also have rounded termination ends 29a as shown in FIGS. 3 and 5 or pointed termination ends (not shown). The through slots 29 provide resiliency to the first end 23 of the collet 18 without sacrificing durability. The interior surface 31 of the collet 18 is essentially smooth except for a shelf 32 equally positioned on each tang 28 at the mid-section 27 for reasons to be discussed further.

Figure 4:
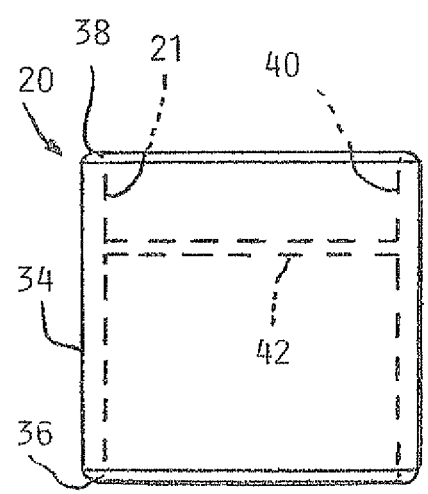
FIG. 4 is a sectional view of a sleeve for the current barb clamp.

Looking at FIG. 4, the sleeve 20 has a smooth exterior annular surface 34. The sleeve 20 has a first or bottom end 36 forming an arcuate base to facilitate assembly to the collet 18. The interior surface 40 forms a slight outward taper at the second or top end 38 of the sleeve 20. The interior surface 40 is essentially smooth throughout the length of the sleeve 20 except for an annular projection 42 that extends from the inner surface. The annular projection 42 is sized and positioned on the sleeve 20 for disposition within the annular groove 26 of the collet 18 to form a lock when the barb clamp 10 is engaged. Therefore, the annular projection 42 is positioned proximate to the second or top end 38 of the sleeve 20.

The sleeve 20 is first placed over the end of the tube 14 so that the second or top end 38 of the sleeve 20 is spaced furthest away from the tube end the collet 18 is then placed on the tube 14 so that the first end 23 of the collet 18 is closest to the sleeve 20. The expanded end 16 of the barbed fitting 12 is then placed into the tube 14. The expanded end 16 of the barbed fitting 12 is sized for being snugly received within the interior of the tube 14. The collet 18 is then slid over the tube 14 having the expanded end 16 of the barbed fitting 12 therein. The shelves 32 located on the interior surface 31 of the collet 18 is a retainer which forms a radial 360° compression around the tube 14 and under the expanded end 16 of the barb fitting 12 so that the barb fitting 12 cannot easily move out of the tube 14. The sleeve 20 is then slid over the collet 18 such that the first or bottom end 36 of the sleeve 20 initially encounters the first end 23 of the collet 18. As the sleeve 20 moves over the collet 18, the tangs 28 on the collet 18 are pushed radially inwardly into the tube 14 and barbed fitting 12, so that the annular shelf 32 of the collet 18 is pressed inwardly into the tube 14 and barbed fitting 12 to provide a tight seal therebetween and thereby lock the annular shelf 32 under the barb 16. The sleeve 20 continues over the collet 18 until the annular projection 42 on the interior surface 40 of the sleeve 20 sits within the annular groove 26 of the collet 18. The small ledges 30 on the exterior surface 34 of the collet 18 provides a stop and lock to prevent the annular projection 42 from moving out of annular groove 26. The barb clamp 10 "clicks" when the collet 18 and sleeve 20 lock together. The barb clamp 10 can then only be removed with the aid of a tool so that disconnection and leakages are prevented.

Figure 6:
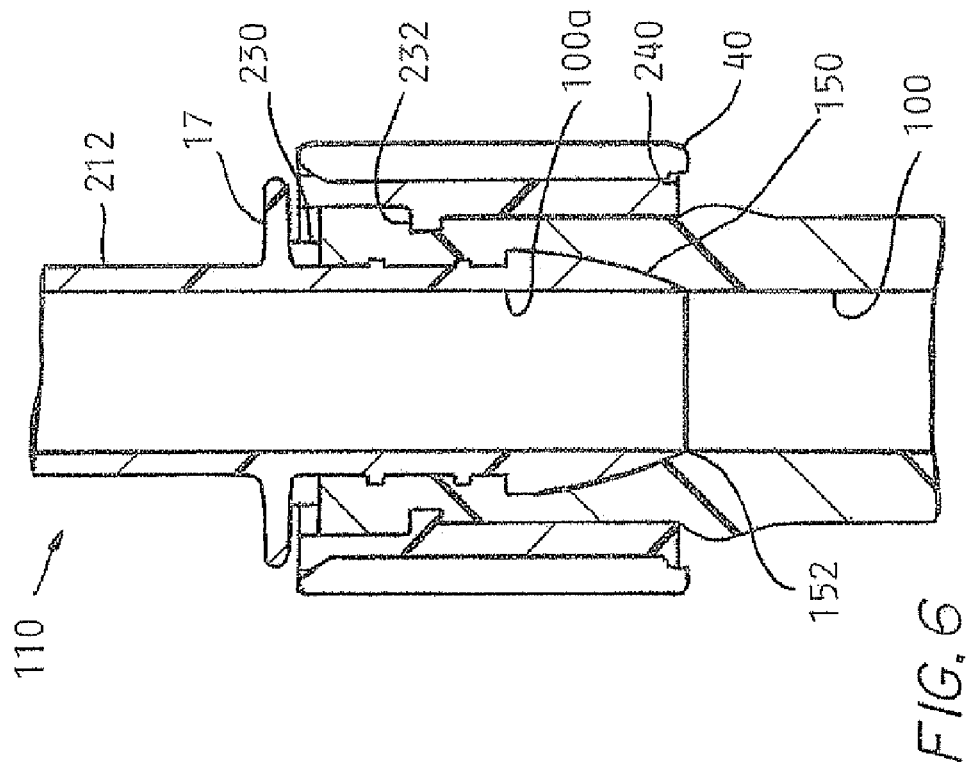
FIG. 6 is a sectional view of an alternative embodiment of the improved barb clamp.

The improved barb clamp shown in FIGS. 5 and 6 has many of the same features as discussed with regard to FIGS. 1-4. However, the improved barb clamp 10 further includes an engineered designed barb fitting 112 which is designed to maintain the same cross sectional area of the bore or fluid passageway 100a in the barb clamp 110 as the cross-sectional area of the bore or fluid passageway 100 in the tube 14 outside of the barb clamp 10. The fluid passageway 100 outside of the barb clamp 110 is defined by the inner bore of the tube 14. The fluid passageway 100a in the improved barb clamp 110 is defined by the inner bore of the barb fitting 112, 212. As can be seen in FIGS. 1 and 2, the cross-sectional area of the fluid passageway 100 of the tube 14 is reduced within the barb clamp 10 as shown at 100a in FIG. 1. The free end 50 of the barb fitting 12 in the prior art has a blunt end 52 with a thickness that causes a transition in the cross-sectional area of the fluid passageway 100 as the tubing 14 enters the barb clamp 10 and changes to the fluid passageway 100a. One problem encountered when designing a barb connection is that it is generally necessary to have a smaller cross-sectional area of the bore in the barb fitting 12 in order to insert the barb fitting 12 into the tube 14. However, the improved clamp 10 provides a barb fitting 112, 212 that has essentially the same bore diameter as the tube 14, but can also easily be inserted into the tube 14.

In the improved barb clamp 110, as shown in FIGS. 5 and 6, the barb fitting 112, 212 has an engineered bore size that has the same cross-sectional area as the bore 100 of the tubing 14. When the improved barb fitting 112, 212 are installed into a tube 14, there is no transition between the inner diameter of the tubing 14 and the inner diameter of the fitting 112. As a result, there is no pressure differential on the tubing or in the fluid from outside to inside of the barb clamp 110. Maintaining a constant pressure or a constant velocity of fluid throughout the system may be imperative in certain medical applications. To accomplish this, the free end 150 of the barb fitting 112, 212 are gradually tapered to a sharp point 152. The sharp point 152 on the free end 150 of the barb fitting 112 also allows for easy insertion of the barb fitting 112 into the tube 14. As a result of this configuration, liquid material can never get between the barb fitting 112, or 212, and the tube 14.

FIG. 6 shows an alternative configuration of the barb clamp 110 which still maintains the same inner diameter of the passageway of the tube 14 whether the tube 14 is within the barb clamp or not. In FIG. 6, it is shown that the barb fitting 212 may include a bumper stop 230 which is attached to the flange 17 to act as a separate stop for the tube 14 while the flange 17 defines another stop for the collet 18, 218 and sleeve 20. The collet 218 may also be modified to have a tapered end 240 to correspond with a tapered end 40 of the sleeve. Further the annular shelf 232 of the collet 218 may be reconfigured to extend further into the tube 14 for a sturdier grip.

The collet 18 and sleeve 20 should be made of an FDA approved material if the barb clamp 10 is in a medical or pharmaceutical environment. The material should be resilient. Preferably the collet 18 is made of acetyl, silicon, or polypropylene. The sleeve 20 is preferably made of polycarbonate, silicon, or polypropylene. The components of the improved barb clamp are made of such material as polypropylene that can be sterilized in an autoclave for medical applications. Antimicrobial additives may also be added to the plastic material used in the manufacturing of at least one of the barb connector, collet, and sleeve.

FIGS. 7-11 show an alternative configuration of the barb clamp 310 according to the present invention. The barb clamp 310 of this embodiment is made of the same materials as disclosed in the previous embodiments. Looking first a FIG. 11, a barb clamp 310 is assembled onto a tube 314 for maintaining the tube 314 in fixed connection. The barb connector or fitting 312 has a tubular configuration. The barb connector 312 has a smooth inner bore 313 with a constant diameter therethrough defining a fluid passageway therein. The constant diameter of the inner bore 313 of the barb connector 312 equals the predetermined inner diameter 315 of the flexible tube 314. The barb connector 312 has a first end for disposing into one end of the flexible tube 314. The first end 322 has an outer angular or ramping surface 323 that commences from the inner surface 313 and extends radially outward away from the inner surface 313 defining a sharp point at the terminating end of the first end 322. As a result, the first end 322 of the barb connector 312 has no edge perpendicular to the fluid passageway of the barb connector 312, and there is no pressure differential in the fluid passageway in the tube 314 inside or outside of the barb clamp 310 when installed. The angular surface 323 extends along the entire radial periphery of the first end 322. The angular surface 323 terminates at a barbed point 324 formed along the exterior surface. The barb fitting 312 may also include a flanged portion 326 spaced from the first end 322 which acts as a stop for insertion of the barb connector 312 into the tube 314. The configuration of the pointed first end 322 of the barb fitting 312 provides a constant fluid passage diameter of the tube 314 whether the fluid passageway in the tube 314 is inside or outside of the barb connector 312.

The barb clamp 310 includes a collet 318 and a sleeve 320. The collet 310 and the sleeve 320 are as shown in FIGS. 7-11. In the illustrated embodiment, the collet 318 and sleeve 320 are connected together by frangible tabs 328 as will be discussed hereinafter. The collet 318 is an annular member having a through aperture 319 for receiving the end of the tube 314 therein. The outer surface 330 of the collet 318 has a bi-level configuration wherein the diameter of the outer surface 330a adjacent the first end 332 is less than the diameter of the outer surface 330b adjacent the second end 334. The first and second outer surfaces 330a, 330b are separated and defined by a ledge 336 positioned at the midpoint of the collet 318.

The interior surface 319 of the collet 318 has an essentially smooth radial surface except at the first end 332, wherein an annular ridge 338 is positioned. The annular ridge 338 is defined by a lead-in annular surface 340 that angles inwardly to the reduced diameter of the ridge 338. The angle leading edge 340 facilitates the entry and assembly of the barbed end 322 of the connector 312 and tube 314. The second end 334 of the collet 318 has a radial surface perpendicular to the fluid passageway. A plurality of the frangible tabs 328 are connected to and extend from the radial surface 334 of the second end. Opposing ends of the frangible tabs 328 are also connected to an inner surface of the sleeve 320 as will be discussed hereinafter.

Elongate through slits 342 commence at and are opened to the first end 332 of the collet 318. The plurality of slits 342 are equally spaced along the circumference of the collet 318. The slits 342 have elongated lateral edges 343a 343b that are spaced from each other forming a gap therebetween. The slits 342 extend approximately two-thirds of the axial length way into the body of the collet 318 from the first end 332. By example only, the slits 342 are positioned directly in alignment with the frangible tabs 328.

The second end 334 of the collet 318 also includes a plurality of through slits 344. The slits 344 are configured the same as the slits 342. The slits 344 also include lateral spaced edges 345a, 345b. The slits 344 extend and are opened to the second end 334 of the collet 318 and extend two-thirds of the axial length into the body of the collet 318. The slits 344 are equally spaced between adjacent slits 342. Therefore, there is a center portion of the collet 318 into which both sets of slits 342, 344 extend. The slits 342,344 allow for a resilient seal around the tube 314 when the barb clamp 310 is in a locked position.

The sleeve 320 has a smooth exterior surface 350. The interior surface 351 of the sleeve has a radial lip 352 formed at the first end 354 of the sleeve. The interior surface 351 has an expanded radial section 358 adjacent to the lip 352. The expanded section 358 has an expanded radial diameter for accommodating the second section 330b of the exterior of the collet 318 when the barb clamp is in the locked position. The expanded section 358 terminates at a ledge 360 defined by a reduced diameter portion 362. Axially, the reduced diameter portion 362 is followed by a ramped portion 364 that ramps outwardly to an expanded end portion 366. The expanded end portion 366 is adjacent to the second end 356 of the sleeve 320. Opposing end portions of the frangible tabs 328 are positioned and connected to the wall of the interior expanded end portion 366 of the sleeve. The connection of the frangible tabs 328 to the collet 318 and sleeve 320 form a gap 329 between the second end 356 of the sleeve 320 and the second end 334 of the collet 318 so that the frangible tabs 328 are the only connection between the collet and sleeve when the barb clamp is in the unlocked position. The position of the frangible tabs 328 relative to the collet 318 and sleeve 320 allow for breakage of the frangible tabs 328 from the collet 318 with a predetermined applied force.

For installation, the attached collet 318 and sleeve 320 are slipped onto the end of the tube 314 with the sleeve 320 end placed on the tube 314 first. The barb fitting or connector 312 is inserted into the end of the tube 314 leading with the pointed barbed end 322. Once the barb connector 312 is tightly installed into the end of the tube 314, the collet 318 is slid back over that end of the tube 314 enclosing both the end of the tube 314 and the barb connector 312. A locking instrument can be used to break the frangible tabs 328 to detach the sleeve 320 from the collet 318 and slide the sleeve 320 over collet 318. Although the tabs 328 are broken away from the collet 318, the portions of the tabs 328 on the inside surface 366 of the sleeve remain in tact and connected to the sleeve 320.

Figure 10:
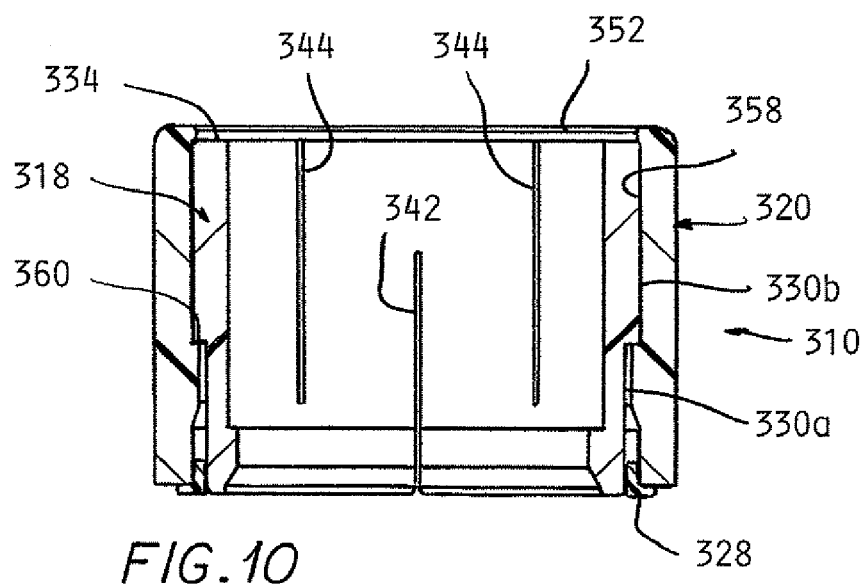
FIG. 10 is a sectional view of the collet and sleeve shown in FIG. 7 in the locked position.
Figure 11:
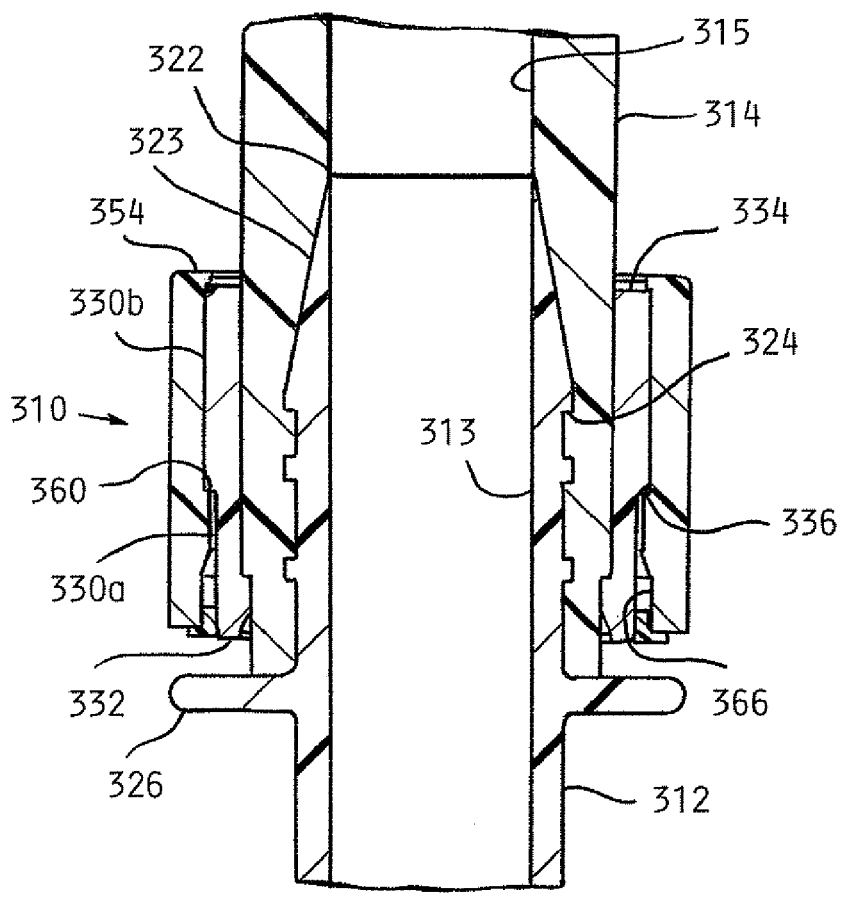
FIG. 11 is a sectional view of the barb clamp shown in FIG. 10 locked onto a tube.
Figure 12:
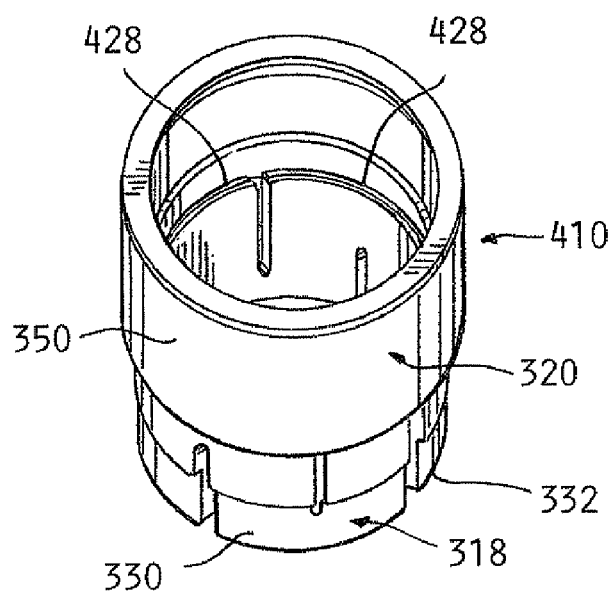
FIG. 12 is a perspective view of another alternative embodiment of the improved collet and sleeve.
Figure 13:
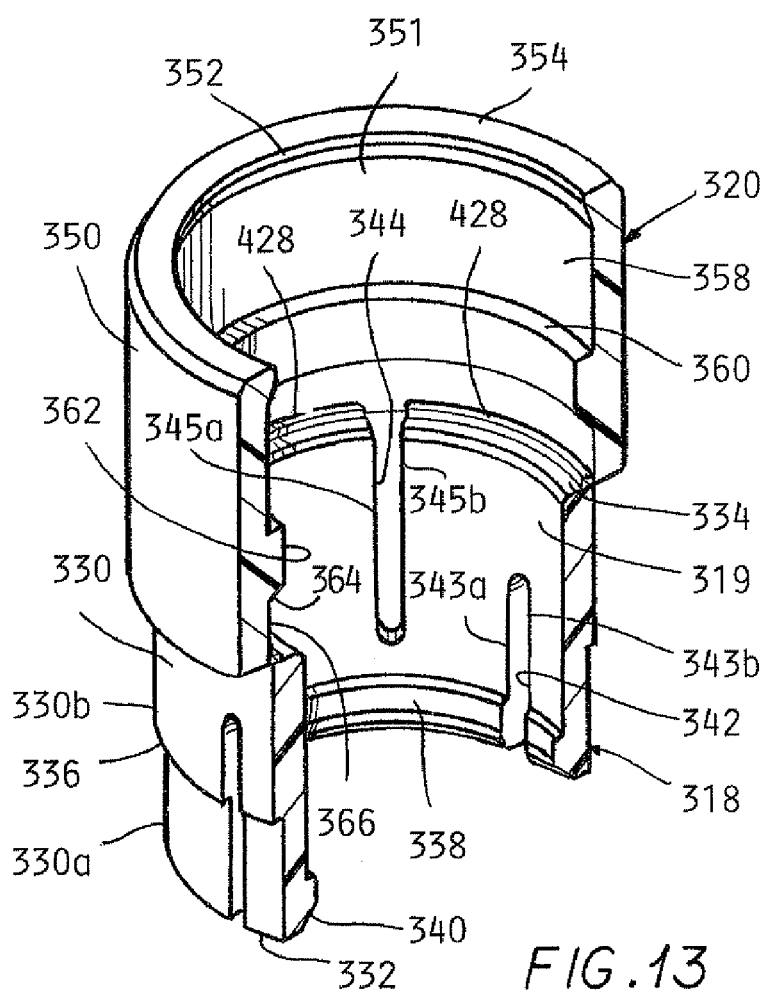
FIG. 13 is a perspective view of the embodiment shown in FIG. 12 having a portion sectioned off to illustrate certain figures.
Figure 14:
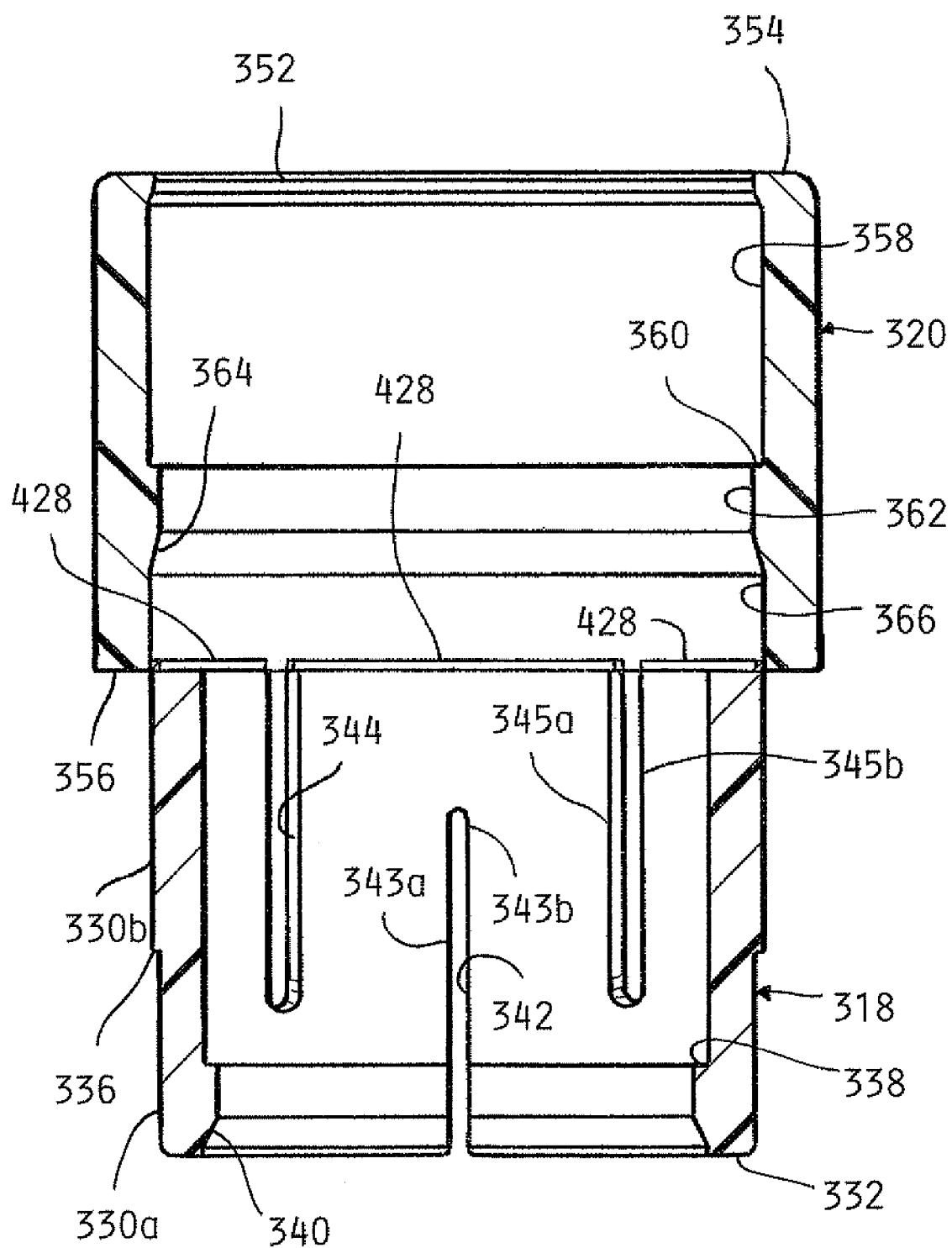
FIG. 14 is a sectional view of the collet and sleeve of the barb clamp shown in FIG. 12 in an unlocked position.
Figure 15:
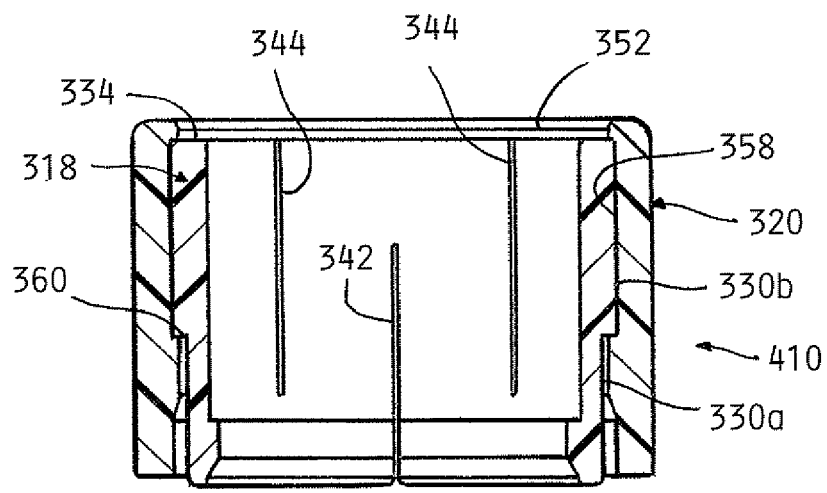
FIG. 15 is a sectional view of the collet and sleeve shown in FIG. 12 in the locked position.
Figure 16:
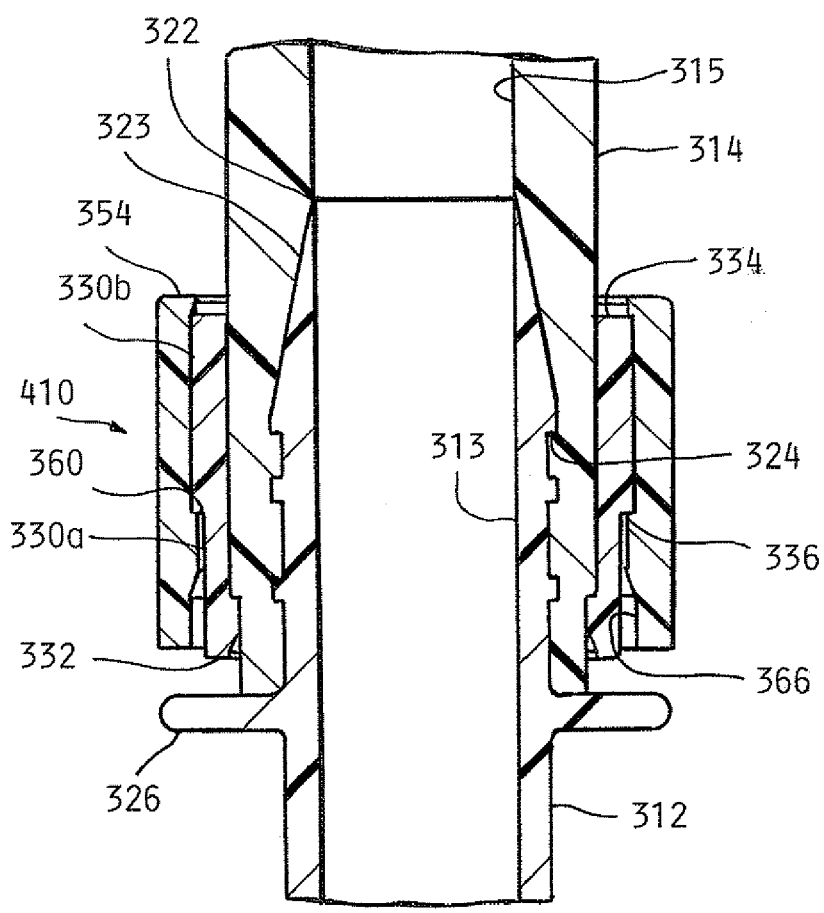
FIG. 16 is a sectional view of the barb clamp shown in FIG. 15 locked onto a tube.

As the sleeve 320 moves over the collet 318, the second end 334 of the collet 318 breaks off the frangible tab portions 328 attached to the inner surface 362 of the sleeve 320. As the sleeve 320 continues its axial movement over the collet 318, the second end 334 of the collet follows the ramp 364; and the slits 344 squeeze together eliminating the gap between the side edges 345a, 345b to provide a resilient seal around the tube 314. The sleeve 320 continues to move over the collet 318 until the second end 334 of the collet 318 is locked and abuts below the radial lip 352 in the sleeve. The radial lip 352 stops further axial movement of the sleeve 320 relative to the collet 318. In the locked position as shown in FIGS. 10 and 11, the second outer surface 330b of the collet 318 is adjacent to the expanded section 358 in the sleeve 320.

The ledge 336 on the collet 318 snaps over and is held on the inner ledge 360 of the sleeve 320. The reduced diameter portion 362 of the sleeve 320 contracts the first section 330a of the collet 318 and removes the gap between the side edges 343a and 343b of the slit 342. The reduced section 362 is positioned to affect the contraction of each of the gaps 342 and 344. The tab portions 328 that remain connected to the sleeve 320 grip the outer surface 330a of the collet 318 adjacent to the first end 332. When the sleeve 320 is locked over collet 318, the barb fitting 312 and the tube 314, there is a 360° radial compression connection of the tube 314.

FIGS. 12-16 show an alternative configuration of a barb clamp 410 according to the present invention. The barb clamp 410 of this embodiment is similar in structure to the embodiment illustrated in FIGS. 7-11 and can be made of the same materials as disclosed in the previous embodiments. Features in this embodiment which are similar to features already discussed with reference to the embodiment of FIGS. 7-11, are referenced using the same numerals and are not discussed in further detail. Unlike the embodiment illustrated in FIGS. 7-11, this embodiment does not contain frangible tabs.

In the illustrated embodiment in FIGS. 12-16, the collet 318 and sleeve 320 are connected together by a frangible meniscus of material 428. The frangible meniscus 428 can be connected to and extend from the radial surface of the second end 334 of the collet 318. Unlike the connection of the frangible tabs 328 illustrated in FIGS. 7-11, frangible meniscus 428 can extend through the entire length of radial surface 334. Alternatively, frangible meniscus can extend to only a portion of the length of radial surface 334.

Opposing end portions of the frangible meniscus 428 can be positioned and connected to the wall of the interior expanded end portion 366 of the sleeve. Alternatively, frangible meniscus can be positioned and connected to a radial surface of the end portion 366 of sleeve 210. Frangible meniscus 428 can be the only connection between the collet and sleeve when the barb clamp is in the unlocked position. The position of the frangible meniscus 428 relative to the collet 318 and sleeve 320 allow for breakage of the frangible meniscus 428 from the collet 318 and sleeve 320 with a predetermined applied force.

The frangible meniscus 428 can be made of any suitable material that permits the sleeve 320 and the collet 318 to remain intact while in the unlocked position and permits the sleeve and collet 318 to break away from one another while in the locked position. For example, the frangible meniscus 428 can be made of thin webs of plastic or the like.

For installation, the attached collet 318 and sleeve 320 are slipped onto the end of the tube 314 with the sleeve 320 end placed on the tube 314 first. The barb fitting or connector 312 is inserted into the end of the tube 314 leading with the pointed barbed end 322. Once the barb connector 312 is tightly installed into the end of the tube 314, the collet 318 is slid back over that end of the tube 314 enclosing both the end of the tube 314 and the barb connector 312. A locking instrument can be used to break the frangible meniscus 428 to detach the sleeve 320 from the collet 318 and slide the sleeve 320 over collet 318 to attain a 360° radial compression connection of the tube 314. The frangible meniscus 428 can be broken away from both the collet 318 and the sleeve 320. Alternatively, the frangible meniscus can remain intact to at least one of the collet 318 and the sleeve 320.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A barb clamp for a flexible tube having a predetermined inner diameter defining a passageway therein and an outer surface, the clamp comprising:
    a barb connector having a tubular configuration with a first end for disposing within an end of the tube, the barb connector having a smooth inner bore with a constant diameter defining a fluid passageway therein, the constant diameter of the inner bore equal to the predetermined inner diameter of the flexible tube;
    a cylindrical collet having a through aperture slidable over the first end of the barb connector, the collet having a first end, a second end, and inner and outer surfaces, the inner surface of the collet having a circumferential ridge at the first end of the through aperture, the outer surface of the collet having a bi-level configuration wherein the diameter of the outer surface adjacent the first end is less than the diameter of the outer surface adjacent the second end defining a ledge therebetween; and
    a cylindrical sleeve having a through center aperture for slidably receiving the collet, the sleeve having a first and a second end, the second end of the sleeve connected to the second end of the collet by a frangible meniscus of material, the through center aperture of the sleeve defined by an inner surface, the inner surface having a first circumferential portion, a second circumferential portion, a third circumferential portion and a fourth circumferential portion, the first circumferential portion having an expanded diameter and located adjacent to the second end of the sleeve, the frangible meniscus connected to the first circumferential portion, the second circumferential portion located adjacent to the first circumferential portion and ramping to a reduced diameter portion defined by the third circumferential portion, the third circumferential portion terminating at a ledge at a midpoint of the sleeve.

2. The barb clamp of claim 1, wherein the outer surface of the first end of the barb connector is radially angled to define a ramp to a barbed end, the ramp terminating at the barbed end and forming a sharp point at the first end of the barb connector.

3. The barb clamp of claim 2, wherein the first and second ends of the collet have through slits formed therein, the through slits defined by lateral edges having a gap therebetween, and wherein the through slits at the second end are offset with the slits at the first end.

4. The barb clamp of claim 3 wherein the slits extend from and are open to their respective ends and extend approximately two thirds into the axial length of the collet.

5. The barb clamp of claim 1, wherein the frangible meniscus is made of thin plastic material.

6. The barb clamp of claim 1, wherein the ledge formed in the inner surface of sleeve receives the ledge on the outer surface of the collet when the barb clamp is in a locked position.

7. The barb clamp of claim 1, wherein the fourth circumferential portion commences at the ledge and extends to a radial lip at the first end of the sleeve.

8. The barb clamp of claim 7, wherein the radial lip defines a stop for axial movement of the collet relative to the sleeve.

9. The barb clamp of claim 1, wherein the frangible meniscus breaks away from at least one of the sleeve and the collet when the barb clamp is in a locked position.

10. The barb clamp of claim 1, wherein the collet has a flat surface positioned perpendicularly at the second end and one end of the frangible meniscus is connected to the flat surface and the other end of the frangible meniscus is connected to the first circumferential portion.

11. The barb clamp of claim 10, wherein the other end of frangible meniscus of material is connected to at least one of an inner surface of the first circumferential portion and a radial surface of the first circumferential portion.

12. The barb clamp of claim 10, wherein the frangible meniscus of material is connected to substantially the entire length of the flat surface.

* * * * *